United States Patent [19]

Flannery et al.

[11] 3,992,624
[45] Nov. 16, 1976

[54] APPARATUS AND METHOD OF X-RAY TOPOGRAPHY AT CRYOGENIC TEMPERATURE

[75] Inventors: Robert E. Flannery, Alexandria; Paul LoVecchio, Reston, both of Va.

[73] Assignee: The United States of America as represented by the Secretary of the Army, Washington, D.C.

[22] Filed: Apr. 29, 1975

[21] Appl. No.: 572,764

[52] U.S. Cl. .............................. 250/273; 250/275; 250/277 CH
[51] Int. Cl.² ...................................... G01H 23/20
[58] Field of Search ........... 250/272, 273, 274, 275, 250/277 CH

[56] References Cited
UNITED STATES PATENTS

| 3,390,267 | 6/1968 | Deminet | 250/277 CH |
| 3,751,662 | 8/1973 | Grienauer | 250/277 CH |
| 3,839,635 | 10/1974 | Chan | 250/277 CH |
| 3,855,469 | 12/1974 | Pluchery | 250/272 |
| 3,860,815 | 1/1975 | Hall | 250/277 CH |

*Primary Examiner*—Craig E. Church
*Attorney, Agent, or Firm*—Nathan Edelberg; Max L. Harwell; Robert P. Gibson

[57] ABSTRACT

A method of x-ray topography of crystals at cryogenic temperatures which does not require continuous pumping of the sample chamber during low-temperature operation. The method eliminates the problems of vibrations degrading the high-resolution photographic image recorded and also prevents loss of the sample's angular alignment with the x-ray beam caused by torques produced by a vacuum-coupling mechanism.

10 Claims, 13 Drawing Figures

APPARATUS AND METHOD OF X-RAY TOPOGRAPHY AT CRYOGENIC TEMPERATURE

The invention described herein may be manufactured, used, and licensed by or for the Government for governmental purposes without the payment to us of any royalty thereon.

BACKGROUND OF THE INVENTION

X-ray analysis of materials has been used as an analytical tool many times during the last few decades. Conventional x-ray diffraction has been performed both at high temperatures and at cryogenic temperatures, particularly for the study of phase transformations by observation of changes in lattice parameters. Such techniques involve diffraction from a limited area of the sample. Subgrains within this limited area can contribute to the half-width of the diffracted peak. analysis of rocking curves can give information about the angles of subgrains. However, an observer does not know the actual shape and distribution of the subgrains but only that they are present. X-ray topography, however, is a method of x-ray analysis that yields a picture of the sample surface with the subgrains actually delineated. In the Berg-Barrett topographic method, a divergent beam floods the crystal surface at a small incident angle.

A high-resolution photographic plate is placed as close as possible to the sample surface to record the image produced by the x-ray beam diffracting from the sample surface. The Lang method of x-ray topography involves using a highly collimated x-ray beam, thus precluding the possibility of illuminating the entire sample surface at one time. The Lang camera provides a means of translating the sample and photographic plate back and forth relative to the x-ray beam, thus scanning the entire surface. For the Lang technique, the spatial resolution of the recorded image does not depend critically on the sample-to-plate distance, since the beam is highly collimated, unlike the diverging beam of the Bert-Barrett technique.

Conventional x-ray diffraction experiments, when performed on samples maintained at cryogenic temperatures, require continuous pumping of an evacuated chamber to eliminate heat transfer by conduction. Such experiments often require a somewhat bulky sample chamber. The vacuum pump hose must, of course, be connected to the chamber to be evacuated. This type of arrangement is not suitable for x-ray topography for a number of reasons. For Lang x-ray topography, the sample must be capable of translational movement relative to the x-ray beam, and hence the entire sample chamber must be translated during the scanning process. The vacuum pump hose would produce a torque which would tend to rotate the sample relative to the x-ray beam, thus destroying the critical angular alignment of the sample with the x-ray beam. In addition, the vacuum pump vibrations would be transmitted to the sample chamber by the vacuum pump hose. These vibrations would be sufficient to degrade the resolution of the topographic image produced by either the Berg-Barrett method or the Lang technique used in the reflection mode. In addition, the samle chamber vibrations would make it very difficult to place the photographic plate within a millimeter of the sample, as requred for the Berg-Barrett technique of x-ray topography.

SUMMARY OF THE INVENTION

The cryogenic temperature x-ray topography apparatus and method of this invention is unique in that it permits x-ray topographs to be taken of crystals cooled to 77° Kelvin. The method can also be used to measure lattice parameter change at various locations on the cooled sample since the sample can be translated relative to the incident X-ray beam. This translation is not easily attained with conventional x-ray equipment used at cryogenic temperatures.

The method makes possible the observation of elastic strain produced by cooling various crystal-substrate combinations to cryogenic temperatures. such information can be used in choosing detector-substrate combinations which will optimize infrared detector performance.

In operation, a dewar and sample mount box assembly is used as the sample mount on a Lang camera used in the Bragg reflection mode for x-ray topography. The assembly may also be used at room temperature so that topographs made at room temperature and 77° Kelvin can be compared.

DETAILED DESCRIPTION OF THE PREFERRED EMBODIMENT

The present method of x-ray topography involves the Bragg diffraction condition. For x-ray diffraction to occur, the Bragg diffraction condition, $$n\lambda = 2d\sin\theta \qquad (1)$$

must be satisfied, where $\lambda$ is the wavelength of the x-ray radiation used, $d$ is the interplanar spacing of the diffracting planes, and $\theta$ is the Bragg angle for diffraction from the particular set of planes. If $\lambda$ and $d$ are fixed, then sin $\theta$, and hence $\theta$, must also be fixed. For a copper x-ray target, the wavelength of the characteristic $K\alpha_1$ line is 1.54051 Angstroms.

Figure 1:
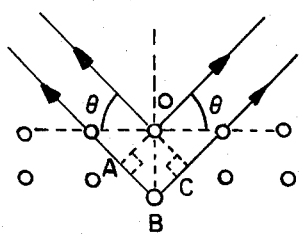
FIG. 1 is a schematic diagram depicting the Bragg angle.

With reference to FIG. 1, the origin of the Bragg equation is hereby discussed. Consider an x-ray beam with wavelength $\lambda$ incident on the planes with interplanar spacing $OB=d$. The difference in path length between parallel wavefronts of the two rays is given by

| Difference in path length | = | AB + BC |
|---|---|---|
| | = | $d\sin\theta + d\sin\theta$ |
| | = | $2d\sin\theta$ |

For constructive interference to occur, this difference in path length must be an integral number of wavelengths. Hence, $$n\lambda = 2d\sin\theta, \quad (2)$$

where $n = 1, 2, 3 \ldots$

The integer $n$ can be incorporated in the interplanar spacing by defining $d_{hkl} = d/n$. This gives, $$\lambda = 2d_{hkl}\sin\theta. \quad (3)$$

Figure 2:
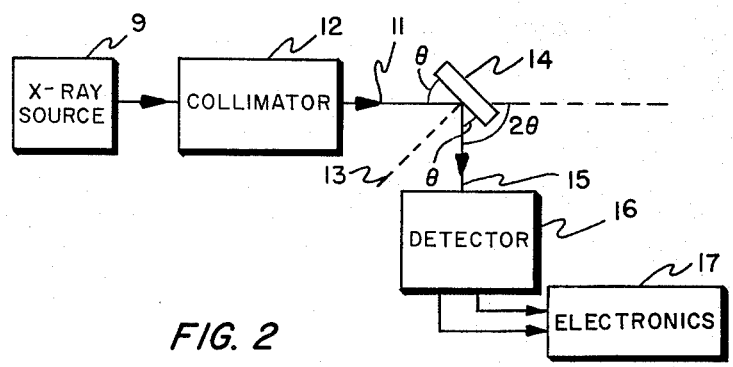
FIG. 2 illustrates a block diagram of a Bragg diffractometer.

Refer now to FIG. 2 for a discussion of the apparatuses used that are in the present method. If a monochromatic x-ray beam from x-ray source 9 is incident upon a single crystal of some material 14, such as lead-tin telluride and the Bragg condition is satisfied, there will be a diffracted beam reflected therefrom. The diffracted beam is detected with a scintillation detector 16. Detector 16 may be made of thallium-activated sodium iodide. The crystal sample planes are aligned to satisfy the Bragg condition. That is, the detector is set at the angle $2\theta$ corresponding to twice the Bragg angle and the sample is rotated independently about an axis perpendicular to the plane containing the incident and diffracted beam. This "fine-tuning" process of rotating the sample is used to set the sample so that the signal from the scintillation detector is maximized. The maximized signal is observed on a chart recorder rate meter 17 connected to the output of detector 16. Dashed line 13 represents the normal to the crystal 14 diffracting plane. A beam collimator 12, may be inserted between source 9 and crystal 14 to provide a collimated incident beam 11 and thus a collimated diffracted beam 15. X-ray source 9 may be, but is not limited thereto, a Jarrell-Ash Multifocus X-ray Generator, Catalog No. 80-000. Collimator 12 has a 150-micron width slit running in the vertical direction that is positioned about 42 centimeters from the focal spot of the x-ray beam. The collimator has an upper and a lower moveable beam stops that adjust the vertical length of the slit such that vertical divergence of the x-ray beam is limited to the extent that the full vertical length of the crystal sample is irradiated. The 150-micron width of the slit as suggested is wide enough to allow full use of $K\alpha_1$ intensity but narrow enough to exclude $K\alpha_2$ radiation.

Figure 3:
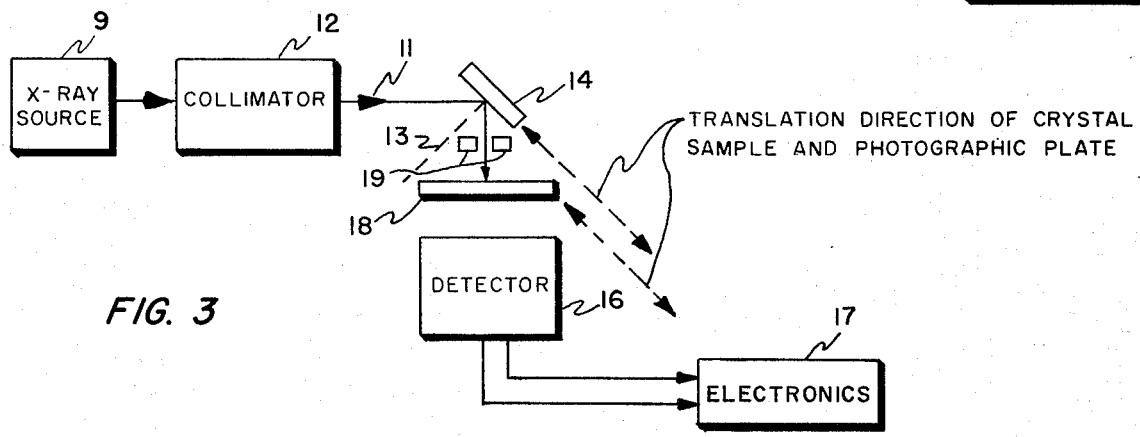
FIG. 3 illustrates a schematic arrangement of a Lang camera used in the Bragg reflection mode for x-ray topography.

The Lang camera depicted in FIG. 3 permits sample 14 to be translated along a direction parallel to the sample surface. A small translational geared motor (not shown) moves the sample 14 and the photographic plate 18 in the same translational direction. The direction of travel is shown by dashed arrow-head lines. The incident x-ray beam will always travel the same distance in space, but it will "see" different areas of sample 14 as the sample is translated. Similarly, the diffracted beam will emerge from the same point in space and travel to the translating photographic plate 18, exposing the width of the photographic plate 18 simultaneously with the x-ray beam sweeps of sample 14. The limits of travel of the Lang camera are determined by observing when the signal on the chart recorder 17 drops down to a background level indicating that the edges of sample 14 have translated beyond the path of incident beam 11. Microswitches controlling the motor are set to reverse the scan direction when the signal drops. During the initial alignment of the sample the scan rate is ¼ inch per minute. After alignment, the photographic plate 18 is mounted on the same translational platform, or specifically disc 52 which forms a part of the platform and will be discussed hereinbelow. The motor is geared to a scan rate of 1 inch per hour while the x-ray topograph is being recorded on plate 18. Photographic plate 18 is placed perpendicular to the diffracted beam, and the plate is also translated parallel to the sample surface. A variable-width diffracted beam slit 19, comprising two closely-spaced plates, is positioned between sample 14 and photographic plate 18. The plates of slit 19 are positioned perpendicular to beam 15 and are stationary. There will then be a 1:1 correspondence between the area of the recorded image on plate 18 and the area of the crystal 14 surface. The exposure time is selected to permit 10 to 20 traverses of the x-ray beam across the translating sample. With detector 16 and slit 19 stationary and sample 14 and photographic plate 18 translating the diffracted beam sweeps through slit 19 covering from one side of plate 18 to the other while the x-ray incident beam sweeps across the sample 14.

If the x-ray beam has a vertical extent so that the entire sample height is illuminated, then the recorded image will be 2-dimensional, rather than linear. The x-ray source 9 actually emits a cone of radiation which is collimated before the beam strikes the sample. The horizontal divergence of the sample is limited by the 150-micron width of the slit. The vertical divergence of the beam is adjusted by setting adjustable beam stops at the top and bottom of the collimator so that the entire sample height is illuminated. The vertical extent of the beam is verified by holding a fluorescent screen in front of the sample and observing the height of the ribbon-shaped beam. The rays are essentially parallel because the long source-to-slit distance, which is about 42 centimeters, allows a half-inch high sample to be completely illuminated with x-rays having vertical divergence of less than two degrees. The horizontal divergence is about 0.05°. If the diffracting planes of the sample are parallel to the sample surface, then the angle between the incident beam and the sample surface will be the same as the angle between the sample surface and the diffracted beam. The normal to the diffracting planes bisects the angle between the incident and diffracted beams. The variable-width diffracted beam slit 19 comprises two metallic leafs that are positioned in close proximity to each other so that the slit therebetween is wide enough so that none of the diffracted intensity is lost during the scanning of the crystal face. Width is usually 1 millimeter, but if the crystal has a non-planar surface or if the angle of incidence of the x-ray beam with the crystal surface is quite low then a wider slit becomes necessary. Slit 19 should be placed as close as possible to the translating crystal 14 without the crystal touching slit 19 during translation. The photographic plate 18 is generally a 1 inch × 1½ inch Kodak NTB nuclear track plate that is sealed from the room light in a cassette.

As discussed hereinbelow with reference to FIGS. 6 and 7, quite often it may be desirable to use diffraction planes that are not parallel to the sample surface. This results in a non-symmetric situation in that the two angles described in the paragraph above are no longer equal and the normal to the diffracting planes is not perpendicular to the sample surface as was the case in FIG. 2. The detector is still set to twice the Bragg angle for the appropriate planes and the sample is rotated so that the normal to the diffracting planes bisects the angle between the incident and diffracted beams. Diffraction planes 14a are shown in offset directions on either side of the crystal sample 14 surface. The sum of the incident angle $\alpha$ and diffracted angle $\beta$ however equal $2\theta$, or twice the Bragg angle in both FIGS. 6 and 7.

After the x-ray topograph is taken, the photographic plate 18, which is made of high resolution plate, such as Kodak Type NTB or an Ilford G-5, is developed and may be examined under a microscope (using transmitted light). After this examination the topograph is usually enlarged photographically. The development procedures used are the ones recommended by Kodak and Ilford. The developed plate is then used as a negative to make an 8 × 10 print. The enlargement is then used to identify defects in the sample. The x-ray topograph may show grain boundaries, slip planes, dislocations, impact damage, strain, polishing scratches, and shadows due to irregular surface features. These defects are undesirable for material which is to be fabricated into detectors for use in a cryogenic environment. Often these defects are not visible under an optical microscope, even at high magnification. In particular, polishing scratches may fill in with abrasive, making the surface appear shiny when there is actually damage due to polishing scratches. Also, slip planes may be below the surface, in which case they would not be visible optically, yet they can be detected by x-rays down to the penetration depth of the x-rays, which is usually a few microns. Slip planes can cause decreases in the performance of lead-tin telluride photodiodes.

Figure 4:
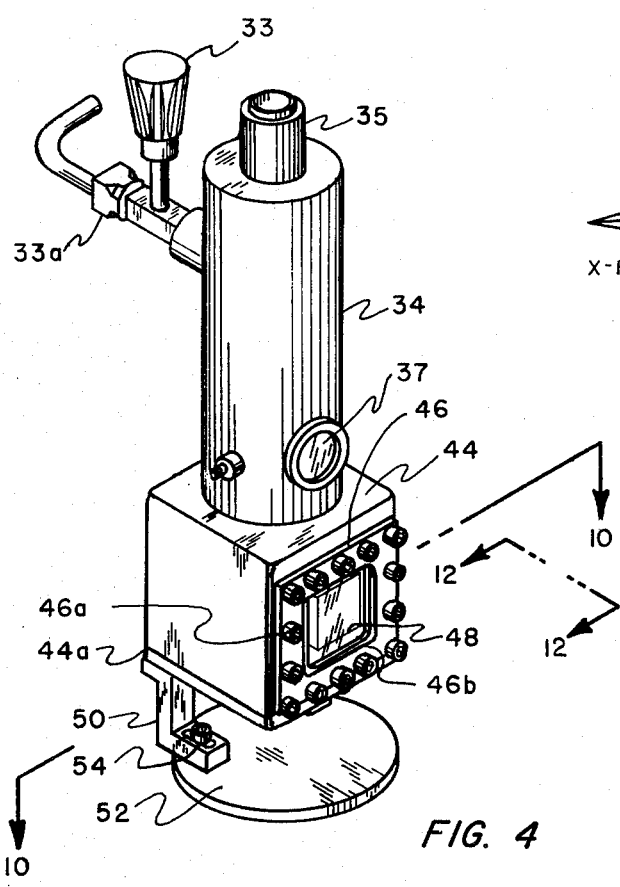
FIG. 4 shows a dewar and the sample mount box assembly of the present invention.
Figure 10:
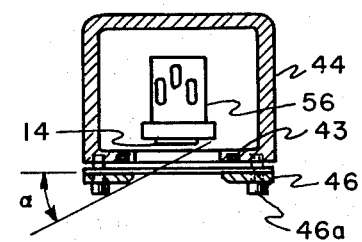
FIG. 10 illustrates a top view of the sample mount and a sectional view of the box with the sample plane in close proximity to the x-ray window.
Figure 11:
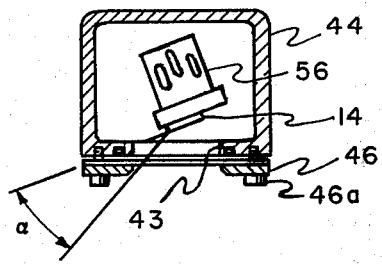
FIG. 11 is the same as FIG. 10 except the sample is offset from the center of the sample mount and the sample orientation is suitable for the x-ray beam to be incident on the sample at a small angle without being intercepted by any protruding parts of the sample mount box.

Refer now to FIG. 4 for an explanation of the dewar and sample mount box assembly. Numeral 34 represents a dewar having an evacuation chamber on the inside portion with a reservoir for pouring cryogenic liquids therein at the upper inside portion. The cryogenic reservoir has a connecting well 35 on top of the dewar for pouring the liquid therein and a cold finger extending down into the evacuation chamber. The bottom of dewar 34 has an opening which fits over an air-tight seal on box 44 in a manner described more fully hereinbelow. The outer case of the dewar 34 may be made of nickel plated brass. Numeral 33a represents a hollow stem passing through the outer case into the evacuation chamber and is adapted for connection to a vacuum pump hose (not shown). Valve knob 33 threads into stem 33a to open the hollow portion of stem 33a when a vacuum is being pulled in the evacuation chamber and to close the hollow portion to hold the vacuum. Dewar 34 is sealed air-tight to box 44 when forced over an O-ring that is inside groove 45a of O-ring holder 45 shown in FIGS. 12 and 13. Box 44 may be made air-tight since it is comprised of a three-sided sheet of metal, such as brass, having upper and lower plates soldered thereto and an x-ray window 48 held firmly against the fourth, or front side. Window 48 is secured to box 44 by a plurality of clamping plate screws 46a passing through clamping plate 46 and threaded into the front side of box 44. A pressure ring 43, shown in FIGS. 10 and 11, provides the air-tight seal since ring 43 fits tightly against window 48 when screws 46a are fully threaded in. These clamping plate screws 46a may be countersunk into plate 46 to avoid blocking x-rays incident beams directed toward the sample being x-rayed and the diffracted beams emitted therefrom. The lower plate of box 44 has two S-shaped legs 50 attached thereto with the lower end of legs 50 screw threaded to 52 by bolts 54 passing through elongated openings in the lower end of legs 50 and threaded into disc 52. Rotatable disc 52 is a portion of a Lang camera. When the dewar and sample mount box assembly has a sample therein and the assembly is rigidly attached to disc 52, the disc can rotate through the full 360° to align the incident x-ray beam with the sample surface in the lateral direction. By adding the desired number of flat washers (represented by 54a in FIG. 13) under legs 50 and then tightening bolts 54 thereover, the sample is tilted from the horizontal for rotational alignment of the sample with the incident x-ray beams. Actually, the working limit of rotation is about 2°, but normally the crystals will not need much alignment about this third axis.

Figure 5:
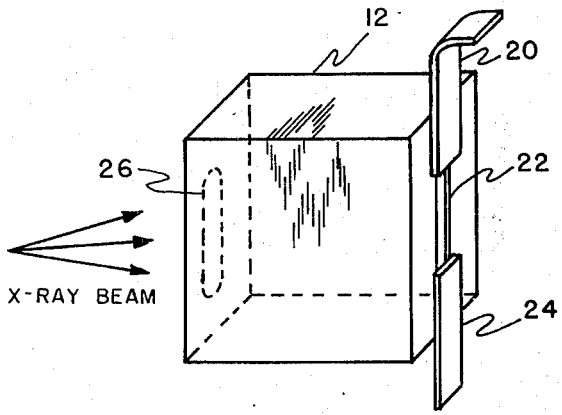
FIG. 5 illustrates one embodiment of an incident beam collimator of the present invention.

FIGS. 5 illustrate the embodiment of the collimator 12. The X-ray beam, shown by directional arrows, from x-ray source 9 is in the configuration of a cone. Therefore, since the desired x-ray beam incident upon sample 14 needs to be a vertical pencil shape, a collimator is needed between source 9 and sample 14. The operation of either of these two collimators is to change the x-ray beam from cone shape to a vertical ribbon of irradiation on samle 14. Looking at FIG. 5, the incoming vertical slot 26 is used for changing the cone into a vertical ribbon beam while traveling through the collimator. An open slit 22 on the output side of collimator 12, about 150-microns wide, is aligned with slot 26. Collimator 12 has an upper beam stop 20 and a lower beam stop 24. Beam stops 20 and 24 slide along a chanel to either open fully or to butt into each other for adjusting the vertical height of the x-ray beam as it exits the collimator.

Figure 6:
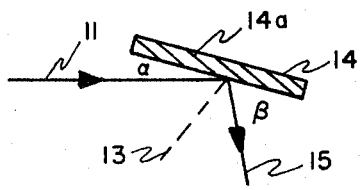
FIGS. 6 and 7 illustrate possible incident and diffracted beams on crystals for diffraction planes that are not parallel to the crystal surface.
Figure 7:
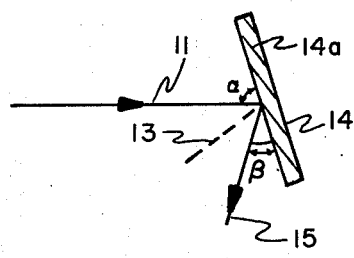

FIGS. 6 and 7 illustrate samples 14 having diffraction planes, represented by 14a, that are not parallel to the sample surface. In these cases, the detector 16 is set to twice the Bragg angle for the appropriate planes 14a and the sample is rotated by rotating the dewar and sample mount box assembly so that the normal to the diffracting plane 14a bisects the angle between the incident and diffracted beams, represented by angles $\alpha$ and $\beta$.

Figure 8:
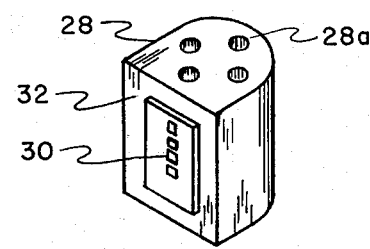
FIG. 8 shows a known sample mount supplied with the dewar prior to addition of the present sample mount box.

FIG. 8 shows a typical sample mount 28 that was attached to the cold finger within the dewar before the addition of the present sample mount box. Infrared radiation enters through the window and the detector's electrical response to the radiation is measured. Window 37 is typically made of barium fluoride. Mount 28 was attached to the cold finger (not shown) with screws passing through the clearance holes 28a and into the tapped holes in the bottom of the coldfinger. Such an arrangement is unsuitable for x-ray topography because of the complete absorption of x-rays by the window. In addition, the window opening is too small for topography and there is no provision for moving the sample close to the window. previously, there was a removable cap with an O-ring seal on the bottom of the dewar 34 for opening to insert the mount therein and then for sealing the cap air-tight for holding a vacuum on the inside volume of the dewar.

Figure 9:
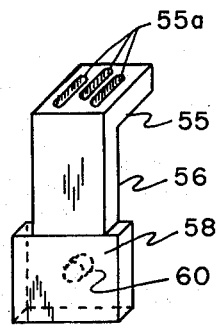
FIG. 9 shows the present sample mount used in making x-ray topographs at cryogenic temperatures.

FIG. 9 illustrates the elongated sample crystal mount 56 which is not to scale, for use in the present dewar and sample mount box assembly. Mount 56 is adapted for attachment to the bottom of the cold finger of dewar 34 by fitting elongated openings 55a against screw-threaded holes in the cold finger and screw threadably connecting sample mount 56 to the coldfinger. With openings 55a being elongated, sample mount 56 may be moved backward and forward before being screw threaded to the coldfinger. The sample is placed on the front face 58 of mount 56. When the sample mount box 44 and dewar 34 are attached together with mount 56 connected to the coldfinger, the dewar 34 may be rotated so that the sample will be adjacent to x-ray window 48. Crystal sample 14 may be attached to the front face 58 in a variety of ways. Some of these ways are by use of a silicon thermal heat sinking compound, double sided Scotch tape, etc. The lighter weight crystals may be mounted with a layer of vacuum or other moderately viscous conductive grease.

Referring now to FIGS. 10 and 11 along with FIG. 4, a top view of mount 56 is shown inside a sectional view of the sample mount box 44. If the incident angle is small due to the diffracting plane of sample 14 being as illustrated in FIG. 6, then the sample mount 56 may have to be moved by rotating dewar 34 through a small angle so that the x-ray incident beam will be able to sweep the entire sample 14 face. In FIG. 10, angle $\alpha$ does not even strike sample 14 at all, but with the sample mount 56 rotated as shown in FIG. 11, the x-ray incident beam $\alpha$ sweeps across the entire sample 14 face.

Figure 12:
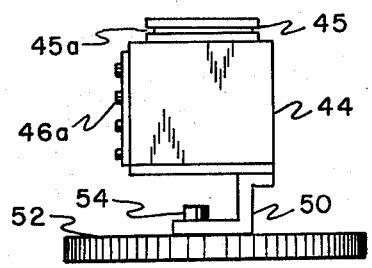
FIG. 12 shows the sample mount box attached by legs to a flat disc on a Lang camera.
Figure 13:
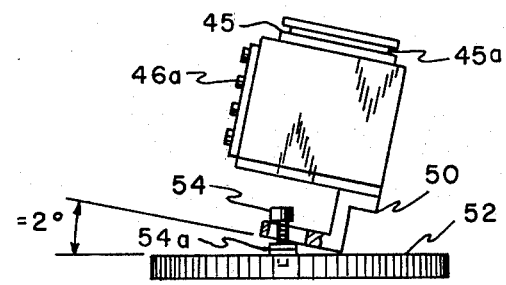
FIG. 13 shows the same setup of FIG. 12 but with flat washers between the legs and the disc for tilting the dewar and sample mount box assembly.

FIGS. 12 and 13 show the sample mount box 44 positioned by legs 50 flat on disc 52 or tilted back by its own weight and being retained by bolts 54 threaded into disc 52 and with flat washers 54a between legs 50 and disc 52. Generally, the tilted position is not required but may be used if needed.

The x-ray window 48 is generally made of 1/32 inch thick semi-transparent material through which an operator can see the sample and through which x-rays can pass. The material suggested for window 48 is polypropylene. Window 48 has tapped clearance holes around its outer periphery which are aligned with tapped clearance holes in the clamping plate 46 and screw-threaded holes in the front of box 44 wherein a plurality of screws 46a may be threadably connected through plate 46 and window 48 to the front of box 44. a pressure ring around the opening in the front of box 44 provides an air-tight seal against window 48 and also to provide bias to prevent bending of the window. The opening in plate 46 through which window 48 is exposed is about 1 inch height and 1½ inches wide. The opening has a 45 degree beveled outer edge. Plate 46 may be made of a metal, such as brass, that is about ⅛ inch thick. window 48 produces some attenuation of x-rays and enables the sample volume inside the box 44 to remain evacuated without excessive bending of the window.

Even though the dewar and sample mount box assembly represented by numerals 34 and 44, that hold sample 14 are not shown in FIGS. 2 and 3, this assembly holds the sample 14 as discussed above. Rotation of sample 14 after the assembly is attached to disc 52 is accomplished by rotating disc 52 of the Lang camera. Further, as represented by dashed lines and arrow heads in FIG. 3, disc 52 and photographic plate 18 mounted on disc 52 translate in the direction of the dashed line. The diffraction beam slit 19 is stationary. Slit 19 is formed by two flat plates with their narrow edges in close proximity to each other with their flat sides being perpendicular to diffracting beam 15. Photographic plate 18 is also perpendicular to beam 15. However, with sample 14 and photographic plate 18 translating together and diffraction beam slit 19 stationary, beam 15 will sweep the width of photographic plate 18 in each translation. Also, the height of beam 15 covers the entire height of sample 14 on each translation. During initial alignment of the sample, the translation scan rate is ¼ inch per minute.

Alignment of crystal 14 on sample holder 56 is as follows before the x-ray topographic shots. The tapped hole 60 in the back center of sample mount face 58 is used to attach sample holder 56 on an x-ray gonimeter. A series of Laue x-ray photographs can then be used to orient sample 14 so that the desired diffraction planes are available. Preferably, the sample 14 should be oriented so that the normal to the diffracting plane lies in the horizontal plane. After the Laue photograph has been taken and any orientation adjustment made to sample 14, the sample holder 56 is then attached to the coldfinger and the bottom of the dewar from which holder 56 protudes are pressed down over an O-ring inside groove 45a of O-ring holder 45 on box 44. After dewar 34 is fitted over box 44, sample holder 56 may be adjusted at the coldfinger prior to placing the window 48 on the front of box 44 such that sample 14 is as close as possible to window 48 without the two touching when window 48 is in place. As discussed above, there will be very little bending of window 48 when vacuum is applied. The cryogenic liquid, generally liquid nitrogen, is not poured through connecting well 35 into the reservoir until a vacuum is applied to the evacuation chamber. Disc 52 sits in a shallow well on top of the Lang camera and is rotatable through 360°. The x-ray source 9 and collimator 12 are in alignment with sample 14 from one direction. Photographic plate 18 may be placed on disc 52 and aligned with diffracted beam slit 19 and detector 16. Disc 52, and plate 18 on disc 52, are translated by a translational geared motor (not shown). X-ray source 9 and collimator 12 may be moved with respect to each other and to sample 14 during initial alignment but are locked down during translation of disc 52. Slit 19 and detector 16 are stationary during translation of sample 14 and photographic plate 18. Source 9 is preferably stationary all the time.

After setting up for the Lang camera x-ray topographic shots as described above, the diffractometer is set at 0° and disc 52 is rotated so that sample 14 surface is parallel to the scanning direction of the Lang camera. The scanning mechanism is rotated so that the scanning direction is parallel to the incident x-ray beam direction. This is the initial "zero alignment," i.e., with everything set at zero the x-ray beam would just graze the sample surface (if it could penetrate the brass box). The detector is set at $2\theta$ and the sample is rotated so that it makes the angle $\alpha$ with the incident beam. The sample is then rotated as necessary to maximize the intensity of the signal obtained from the diffracting planes. After the limit switches and beam stops are set so that the entire sample is scanned, the photographic plate 18 is placed perpendicular to the diffracted beam 15, in front of the detector. The scanning mechanism is activated so that the sample is swept across the beam about 10–20 times at a rate of 1 inch/hour.

A topograph is usually first taken at room temperature to provide a reference and then a second topograph is taken at liquid nitrogen temperature (77° K). It is not necessary to de-mount the sample between topographs, or even to open the air-tight window 48. The entire chamber of the x-ray dewar attachment is evacuated through hollow stem 33a by a vacuum pump (not shown) and then closed by valve 33 then the liquid nitrogen reservoir is filled and refilled until the nitrogen no longer boils off rapidly. This will indicate that the sample holder 56 and sample 14 have reached approximately 77° Kelvin. At this point the initial alignment and "peaking" procedure is repeated as described previously. It is usually necessary to re-pump the dewar in between the time of the topograph taken at room temperature and the time of the topograph taken at cryogenic temperature. The scanning mechanism is then started again in the same manner as the procedure used in taking room-temperature topographs. It is necessary to refill the well of the liquid nitrogen dewar periodically since the hold time is only about 20–25 minutes. This refilling is done by carefully pouring the cryogenic liquid into the connecting well without stopping the scanning motion of the Lang camera.

Obviously, many modifications and variations of the present invention are possible in the light of the above teachings. It is therefore to be understood that within the scope of the appended claims the invention may be practiced otherwise than as specifically described.

Even though slit 19 has been defined as a variable-width diffracted beam slit 19, the preferable language is a scattered radiation limiting means 19. The scattered radiation limiting means 19 is stationary and comprises two closely-spaced plates as defined above that provide a scatter slit for eliminating scattered radiation and spurious reflections from various diffraction planes.

We claim:

1. A method of X-ray topography of a crystal at cryogenic temperatures comprising the steps of:
    providing a dewar having a reservoir at the top and a cold finger at the bottom thermally connected to said reservoir upon which an elongated sample crystal mount is attached with said crystal mounted thereon;
    providing a sample mount box having an O-ring seal surrounding an opening at the top adapted for rotation of said dewar with respect to said sample mount box and adapted for air tight connection to the bottom of said dewar and having a removable X-ray window on a front side wherein said crystals may be manually moved when said X-ray window is open but is air-tight when connected to said sample mounted box and leg supports rigidly connected thereto on a bottom side that are mounted on a rotatable disc of a Lang camera;
    positioning said crystal adjacent said X-ray window and securing said dewar over said O-ring seal on said sample mount box for forming a dewar and sample mount box assembly having an air-tight evacuation chamber when said removable x-ray window is connected on the front side thereof;
    providing an X-ray radiation source and a collimating means in line with an X-ray beam from said X-ray radiation source for providing a collimated vertical incident X-ray beam;
    rotating said rotatable disc upon which said dewar and sample mount box assembly are mounted for aligning said crystal with said collimated vertical incident X-ray beam;
    providing a photographic recording means mounted on said disc in the Bragg reflection mode for recording topographs of the X-ray diffracted radiation from said crystal;
    inserting a scattered radiation limiting means between said crystal and said photographic recording means in which said scattered radiation limiting means is perpendicular to said X-ray diffracted radiation for eliminating scattered radiation and spurious reflections emitted from various diffraction planes in said crystal;
    applying a vacuum to said evacuation chamber then closing an outlet stem to a vacuum pump for holding the vacuum in said evacuation chamber and removing all leads to said vacuum pump to avoid twisting of said dewar during movement of the Lang camera;
    filling said reservoir with a cryogenic liquid until evaporation vibrations cease indicating said crystal is in thermal equilibrium with said reservoir;
    translating said dewar and sample mount box assembly and said photographic recording means along a direction parallel to the surface of said crystal wherein said crystal translates across said collimated vertical incident X-ray beam of radiation and whereby said X-ray diffracted radiation emitted from said crystal passes through said scattered radiation limiting means which is stationary with respect to the translating crystal and photographic recording means and is perpendicular to said X-ray diffracted radiation from said crystal wherein said X-ray diffracted radiation is swept across said photographic recording means for exposure thereof during each translation of said crystal;
    photographically enlarging the exposures of said photographic recording means for visual observation of the resulting X-ray topographs.

2. A method of x-ray topography as set forth in claim 1 wherein said translating means is a small translational geared motor that translates at a scan rate of 1 inch per hour.

3. A method of x-ray topography as set forth in claim 2 wherein said translating means scans said crystal and photographic recording means 10 to 20 times.

4. An apparatus for X-ray topography of a crystal at cryogenic temperatures comprising:
    a dewar and sample mount box assembly connected together to form an air-tight evacuation chamber therebetween wherein said evacuation chamber has a valve controlled hollow stem passing through an outer case of said dewar to a vacuum pump and wherein said dewar has a reservoir at an upper side in which a cryogenic liquid may be poured and a cold finger thermally connected to said reservoir on a lower side extending into said evacuation chamber upon which an elongated sample crystal mount is attached and said crystal is mounted thereon wherein said sample mount box has removable air-tight X-ray window on a front side thereof with said crystal positioned adjacent thereto, with said sample mount box attached to a rotatable disc on a Lang camera;

an X-ray radiation source for producing an incident X-ray beam;

collimating means in line between said X-ray radiation source and said crystal for collimating said incident X-ray beam into a collimated vertical incident X-ray beam whose vertical extent is limited to the full vertical length that said crystal is irradiated by said collimated vertical incident X-ray beam and whose width is wide enough to allow full use of K$\alpha$1 intensity but narrow enough to exclude K$\alpha$2 radiation;

photographic recording means mounted on said rotatable disc on the Lang camera;

means for translating said dewar and sample mount box assembly and said photographic recording means whereby the surface of said crystal is entirely irradiated by said collimated vertical incident X-ray beam on each translation;

a scattered radiation limiting means, said scattered radiation limiting means positioned between said crystal and said photographic recording means perpendicular to diffracted X-ray radiation from said crystal for eliminating scattered radiation and spurious reflections from various diffraction planes within said crystal and wherein said photographic recording means records X-ray topographs of the diffracted X-ray radiation passing through said scattered radiation limiting means and whereby the recorded X-ray topographs may be photographically enlarged.

5. An apparatus for x-ray topography as set forth in claim 4 wherein said x-ray window is made of polypropylene.

6. An apparatus for x-ray topography as set forth in claim 5 wherein said photographic recording means is high resolution plate mounted in a cassette sealed from room light.

7. An apparatus for x-ray topography as set forth in claim 5 wherein said x-ray window is made air-tight by a clamp plate pressed against seals contiguous with said x-ray window with the combination screw threaded to said sample mount box assembly.

8. An apparatus for x-ray topography as set forth in claim 7 wherein said collimating means comprises a 150-micron wide slit positioned at 42 centimeters from the focal spot of said incident x-ray beam from said x-ray radiation source and upper and lower moveable beam stops along said slit for limiting the vertical length of said incident x-ray radiation on said sample.

9. An apparatus for X-ray topography as set forth in claim 8 wherein said means for translating said dewar and sample mount box assembly and said photographic recording means is a small translational geared motor having microswitches for controlling the scan limit and direction and translates said disc on the Lang camera upon which said dewar and sample mount box assembly and said photographic recording means are mounted whereby the translational direction is along a direction parallel to said crystal surface and said collimated vertical incident X-ray beam always travels the same distance between said X-ray radiation source and said crystal.

10. An apparatus for x-ray topography as set forth in claim 9 wherein said scattered radiation limiting means is a variable width scatter slit comprising two stationary closely spaced plates that are positioned perpendicular to said diffracted beam between said crystal and said photographic recording means whereby said diffracted x-ray radiation from the translating crystal simultaneously sweeps across said photographic recording means.

* * * * *